US012751629B2

(12) United States Patent
Ghose et al.

(10) Patent No.: US 12,751,629 B2
(45) Date of Patent: *Oct. 6, 2026

(54) SYSTEM AND METHOD FOR DETECTING RECURRENCE OF A DISEASE

(71) Applicants: GE Precision Healthcare LLC, Wauwatosa, WI (US); The Trustees of Indiana University, Bloomington, IN (US)

(72) Inventors: Soumya Ghose, Niskayuna, NY (US); Zhanpan Zhang, Niskayuna, NY (US); Sanghee Cho, Niskayuna, NY (US); Fiona Ginty, Saratoga Springs, NY (US); Cynthia Elizabeth Landberg Davis, Niskayuna, NY (US); Jhimli Mitra, Niskayuna, NY (US); Sunil S. Badve, Indianapolis, IN (US); Yesim Gokmen-Polar, Noblesville, IN (US); Elizabeth Mary McDonough, Glenville, NY (US)

(73) Assignees: GE Precision Healthcare LLC, Waukesha, WI (US); The Trustees of Indiana University, Bloomington, IN (US)

( * ) Notice: Subject to any disclaimer, the term of this patent is extended or adjusted under 35 U.S.C. 154(b) by 658 days.

This patent is subject to a terminal disclaimer.

(21) Appl. No.: 17/981,913

(22) Filed: Nov. 7, 2022

(65) Prior Publication Data

US 2023/0309836 A1 Oct. 5, 2023

Related U.S. Application Data

(63) Continuation-in-part of application No. 17/710,326, filed on Mar. 31, 2022.

(51) Int. Cl.
*A61B 5/00* (2006.01)
*G06F 18/23213* (2023.01)
(Continued)

(52) U.S. Cl.
CPC ............ *A61B 5/0091* (2013.01); *A61B 5/004* (2013.01); *A61B 5/4312* (2013.01);
(Continued)

(58) Field of Classification Search
CPC . G06T 2207/10132; G06T 2207/20021; G06T 2207/20076; G06T 2207/20081;
(Continued)

(56) References Cited

U.S. PATENT DOCUMENTS

| | | | | |
|---|---|---|---|---|
| 10,380,739 | B2 * | 8/2019 | Vega | A61B 5/0091 |
| 11,574,404 | B2 | 2/2023 | Madabhushi | |

(Continued)

FOREIGN PATENT DOCUMENTS

| | | | | |
|---|---|---|---|---|
| CA | 3025510 C * | 2/2021 | G01N 33/57415 |
| CN | 108597603 A * | 9/2018 | G06F 18/24155 |

(Continued)

OTHER PUBLICATIONS

Burnside ES, Rubin DL, Shachter RD. Using a Bayesian network to predict the probability and type of breast cancer represented by microcalcifications on mammography. Stud Health Technol Inform. 2004;107(Pt 1):13-7. PMID: 15360765. (Year: 2004).*

(Continued)

*Primary Examiner* — Gandhi Thirugnanam
(74) *Attorney, Agent, or Firm* — Fletcher Yoder, P.C.

(57) ABSTRACT

A method for determining a recurrence of a disease in a patient is presented. The method includes generating a plurality of medical images of an organ of the patient and determining a plurality of recurrence probabilities from the plurality of medical images. A recurrence of the disease is
(Continued)

determined based on the plurality of recurrence probabilities and clinicopathological data of the patient using a Bayesian network.

7 Claims, 6 Drawing Sheets

(51) Int. Cl.
*G06T 7/00* (2017.01)
*G16H 50/20* (2018.01)

(52) U.S. Cl.
CPC ............ *A61B 5/7275* (2013.01); *A61B 5/742* (2013.01); *G06F 18/23213* (2023.01); *G06T 7/0012* (2013.01); *G16H 50/20* (2018.01); *A61B 2576/02* (2013.01); *G06T 2207/10116* (2013.01); *G06T 2207/30068* (2013.01); *G06T 2207/30096* (2013.01); *G06V 2201/032* (2022.01)

(58) Field of Classification Search
CPC . G06T 2207/20084; G06T 2207/30024; G06T 7/0012; G06T 2207/10116; G06T 2207/30068; G06T 2207/30096; G06T 2207/10088; G06T 2207/10104; G06T 2207/10024; A61B 5/0091; A61B 5/004; A61B 5/4312; A61B 5/7275; A61B 5/742; A61B 2576/02; A61B 5/055; A61B 5/0035; A61B 5/7267; G06F 18/23213; G16H 50/20; G16H 30/40; G16H 50/30; G06V 2201/032; G06V 20/698
See application file for complete search history.

(56) References Cited

U.S. PATENT DOCUMENTS

| | | | | |
|---|---|---|---|---|
| 11,581,052 | B2 * | 2/2023 | Hashimoto | G11C 16/349 |
| 11,676,703 | B2 | 6/2023 | Vaidya | |
| 11,983,912 | B2 * | 5/2024 | Stumpe | G06V 20/695 |
| 12,019,674 | B2 | 6/2024 | Wang | |
| 12,334,190 | B2 | 6/2025 | Ma | |
| 2007/0099219 | A1 * | 5/2007 | Teverovskiy | G16H 50/50 435/6.16 |
| 2012/0147010 | A1 * | 6/2012 | Schmidt | G06T 11/206 345/440 |
| 2014/0038197 | A1 * | 2/2014 | Waldman | C12Q 1/6886 435/6.12 |
| 2017/0091937 | A1 * | 3/2017 | Barnes | G06V 10/806 |
| 2018/0276498 | A1 * | 9/2018 | Madabhushi | A61B 5/4842 |
| 2018/0336395 | A1 | 11/2018 | Madabhushi | |
| 2019/0087693 | A1 * | 3/2019 | Madabhushi | G06T 7/0012 |
| 2019/0159745 | A1 * | 5/2019 | Madabhushi | A61B 6/5217 |
| 2019/0259156 | A1 | 8/2019 | Madabhushi | |
| 2020/0174000 | A1 * | 6/2020 | Badve | G01N 33/57492 |
| 2020/0315589 | A1 | 10/2020 | Stavros | |
| 2021/0110541 | A1 | 4/2021 | Vaidya | |
| 2021/0169349 | A1 * | 6/2021 | Madabhushi | A61B 5/7275 |
| 2022/0319675 | A1 * | 10/2022 | Mork | G06N 3/0475 |
| 2022/0328134 | A1 | 10/2022 | Ma | |
| 2022/0404364 | A1 * | 12/2022 | Madabhushi | G16H 50/70 |
| 2023/0242992 | A1 | 8/2023 | Lindley | |
| 2023/0307137 | A1 | 9/2023 | Ghose | |
| 2023/0309836 | A1 * | 10/2023 | Ghose | G06V 20/698 382/128 |
| 2023/0317293 | A1 * | 10/2023 | Cho | G16H 30/00 382/100 |
| 2023/0342933 | A1 | 10/2023 | Lou | |
| 2023/0368894 | A1 * | 11/2023 | Kunz | G06T 7/0012 |
| 2024/0347207 | A1 | 10/2024 | Singhal | |
| 2025/0117893 | A1 * | 4/2025 | Steiner | G06T 5/60 |
| 2025/0166828 | A1 | 5/2025 | Hiremath | |

FOREIGN PATENT DOCUMENTS

| | | | | | |
|---|---|---|---|---|---|
| CN | 113160965 | A | * | 7/2021 | G16H 50/70 |
| CN | 113160969 | A | * | 7/2021 | G06F 18/23 |
| CN | 115064270 | A | * | 9/2022 | G06T 7/62 |
| EP | 4224479 | A1 | | 8/2023 | |
| WO | WO-2009114862 | A1 | * | 9/2009 | G01N 33/57415 |
| WO | WO-2015126886 | A1 | * | 8/2015 | C12Q 1/6886 |
| WO | 2022036869 | A1 | | 2/2022 | |
| WO | WO-2022157775 | A1 | * | 7/2022 | A61B 5/7275 |
| WO | 2022221712 | A1 | | 10/2022 | |
| WO | 2025110881 | A1 | | 5/2025 | |

OTHER PUBLICATIONS

Kahn CE Jr, Roberts LM, Wang K, Jenks D, Haddawy P. Preliminary investigation of a Bayesian network for mammographic diagnosis of breast cancer. Proc Annu Symp Comput Appl Med Care. 1995:208-12. PMID: 8563269; PMCID: PMC2579085. (Year: 1995).* https://www.academia.edu/91715252/Using_a_Bayesian_Network_to_Predict_the_Probability_and_Type_of_Breast_Cancer_Represented_by_Microcalcifications_on_Mammography , 2025 (Year: 2025).*

Braman et al., "Association of Peritumoral Radiomics With Tumor Biology and Pathologic Response to Preoperative Targeted Therapy for HER2 (ERBB2)-Positive Breast Cancer." JAMA network open vol. 2,4 e192561. Apr. 5, 2019, 18 pages.

Braman et al., "Intratumoral and peritumoral radiomics for the pretreatment prediction of pathological complete response to neoadjuvant chemotherapy based on breast DCE-MRI." Breast cancer research : BCR vol. 19,1 57. May 18, 2017, 14 pages.

Sali et al., "Deep Learning for Whole-Slide Tissue Histopathology Classification: A Comparative Study in the Identification of Dysplastic and Non-Dysplastic Barrett's Esophagus." Journal of personalized medicine vol. 10,4 141. Sep. 23, 2020, 16 pages.

Sari et al., "Unsupervised Feature Extraction via Deep Learning for Histopathological Classification of Colon Tissue Images," IEEE Trans Med Imaging. May 2019;38(5):1139-1149, 11 pages.

Sedghi et al., "Deep neural maps for unsupervised visualization of high-grade cancer in prostate biopsies." International journal of computer assisted radiology and surgery vol. 14,6 (2019): 1009-1016, 16 pages.

Solin et al., "A multigene Expression Assay to PRedict Local Recurrence Risk for Ductal Carcinoma in Situ of the Breast," JNCI, vol. 105, Issue 10, 10 pages.

Leonard et al., "Association of the 12-Gene Breast DCIS Score® Assay With Local Recurrence in Patients with Ductual Carcinoma In Situ Treated pm Accelerated Partial Breast Radiotherapy Protocols," Frontiers in Oncology, vol. 11, Jun. 2021, 6 pages.

Partridge et al., "Challenges in DCIS Risk Communication and Decision-Making: Report from an American Cancer Society and National Cancer Institute Workshop," National Institute of Health, 2012, 15 pages.

Elmore et al., "Diagnostic Concordance Among Pathologies Interpreting Breast Biopsy Specimens," Department of Health & Human Services—USA, Mar. 17, 2015, 25 pages.

Badve et al., "Ductal Carcinoma in Situ of Breast: Update 2019," Department of Health & Human Services—USA, Oct. 2019, 17 pages.

Afshar et al.; "From Hand-Crafted to Deep Leaming-based Cancer Radiomics: Challenges and Opportunities"; arXiv; arXiv: 1808.07954; pp. 1-31; <https://doi.org/10.48550/arXiv.1808.07954> (Year: 2019).

* cited by examiner

SYSTEM AND METHOD FOR DETECTING RECURRENCE OF A DISEASE

CROSS-REFERENCE TO RELATED APPLICATION

This application is a continuation-in-part Application of U.S. patent application Ser. No. 17/710,326, entitled "SYSTEM AND METHOD FOR DETECTING RECURRENCE OF A DISEASE", filed Mar. 31, 2022, which is herein incorporated.

FIELD

Embodiments of the subject matter disclosed herein relate to medical imaging, and more particularly to breast cancer detection using medical imaging.

BACKGROUND

Breast cancer is the most common cancer in women worldwide, affecting an estimated 1.5 million women around the world each year. It is also a leading cause of cancer-related death in women. Early detection of breast cancer can reduce mortality and the intensity of treatment required. Among the breast cancer subtypes, invasive Triple negative breast cancer (TNBC) (which is stage 1+) is the most aggressive and heterogeneous breast cancer subtype and accounts for 10-20% of newly diagnosed early breast cancers. The lack of hormone receptors and human epidermal growth factor receptor 2 (HER2) prevent TNBCs from being treated with therapies against these targets. Recurrences of TNBC occurs in about 25% of patients and is observed within the first few years after diagnosis. Early detection of recurrence from routinely collected mammograms would allow early intervention and a better treatment procedure.

In many cases, the cancer tumor in a breast is detected by a medical imaging procedure such as a Mammography. In digital mammography, a scout or pre-shot image may be taken of a patient to determine an x-ray technique (e.g., x-ray tube current and voltage, exposure time) to acquire images of the patient having a sufficient brightness. Upon determination of the x-ray technique, one or more x-ray images of the patient may be acquired. In some examples, multiple x-ray images may be acquired at different view angles and/or at different energy levels.

Although, an existing cancer tumor may be detected using the mammography technique, predicting recurrence in TNBC is difficult from routinely collected clinical data including biopsy samples, clinical information, and mammograms. Therefore, there is a need for an improved system and method to determine recurrence for triple negative breast cancer patients.

In addition, ductal carcinoma in-situ (DCIS) is an early stage 0 breast cancer and accounts for 20% of newly diagnosed breast cancer cases. Diagnostically, DCIS needs to be distinguished from other intraductal proliferations (such as usual ductal hyperplasia and atypical hyperplasia) as well as normal ducts and lobules. Local recurrences and/or progression to invasive cancer is a major concern. This results in patients being treated with surgery (e.g., lumpectomy or mastectomy) without or without additional radiotherapy. System anti-estrogenic therapy in the form of tamoxifen is also often recommended. Recurrence and/or progression is observed in 30% of patients with surgery alone. This can be reduced to approximately 10% with the addition of radiotherapy and endocrine therapy.

DCIS patients have an excellent overall survival rate and over-treatment is always a cause for concern due to potential side-effects. Standard clinicopathological factors (e.g. age, growth pattern, tumor size, margin status, grade, etc.) have been shown to have limited value in predicting recurrence and segregation of high and low risk patients. In addition, current tests to determine risk stratification of patients require a significant amount of material for genomic analysis (e.g., Oncotype Dx). However, getting enough sample is difficult since DCIS is often small, thus, it is difficult to perform genomic analysis on DCIS. Therefore, there is a need for early and accurate recurrence prediction to facilitate a more aggressive treatment policy for high-risk patients (e.g., mastectomy or adjuvant radiation therapy), while simultaneously reducing over-treatment of low-risk patients.

BRIEF DESCRIPTION

In accordance with an embodiment of the present technique, a method for determining a recurrence of a disease in a patient is presented. The method includes generating a plurality of medical images of an organ of the patient and determining a plurality of recurrence probabilities from the plurality of medical images. The method further includes determining a recurrence of the disease based on the plurality of recurrence probabilities and clinicopathological data of the patient using a Bayesian network.

In accordance with another embodiment of the present technique, a system including a memory, a display device and a processor communicable coupled to the memory is presented. The processor is configured to generate a plurality of medical images of an organ of the patient and determine a plurality of recurrence probabilities from the plurality of medical images. The processor is further configured to determine a recurrence of the disease based on the plurality of recurrence probabilities and clinicopathological data of the patient using a Bayesian network.

In accordance with yet another embodiment of the present technique, a method for determining a recurrence of a disease in a patient is presented. The method includes generating Hematoxylin and Eosin (H&E) biopsy sample images of the patient and extracting fixed image patches of predefined pixels from the H&E biopsy sample images. The method further includes automatically mapping each of the fixed image patches to an initial latent space and refining the latent space by encoding patches generated by a generative adversarial network (GAN) model that captures features of aggressive cancers. Finally, the method includes using a deep learning (DL) network to predict the first recurrence probability based on the refined latent space.

In accordance with a further embodiment of the present technique, a method for determining a recurrence of ductal carcinoma in situ (DCIS) in a patient is presented. The method includes generating a plurality of medical images of breast tissue of the patient and determining a plurality of recurrence probabilities from the plurality of medical images. The method further includes determining a recurrence of the DCIS based on the plurality of recurrence probabilities and clinicopathological data of the patient using a Bayesian network.

In accordance with a still further embodiment of the present technique, a system including a memory, a display device and a processor communicable coupled to the memory is presented. The processor is configured to generate Hematoxylin and Eosin (H&E) biopsy sample images of breast tissue of the patient and to extract fixed image patches of predefined pixels from the H&E biopsy sample images. The processor is also configured to automatically map each of the fixed image patches to an initial latent space and refine the latent space by encoding patches generated by a generative adversarial network (GAN) model that captures features of aggressive ductal carcinoma in situ (DCIS). Finally, the processor is further configured to use a deep learning (DL) network to predict a recurrence probability of the DCIS based on the refined latent space.

In accordance with an even further embodiment of the present technique, a method for determining a recurrence of ductal carcinoma in situ (DCIS) in a patient is presented. The method includes generating Hematoxylin and Eosin (H&E) biopsy sample images of breast tissue of the patient and extracting fixed image patches of predefined pixels from the H&E biopsy sample images. The method further includes automatically mapping each of the fixed image patches to an initial latent space and refining the latent space by encoding patches generated by a generative adversarial network (GAN) model that captures features of aggressive DCIS. Finally, the method includes using a deep learning (DL) network to predict a recurrence probability of the DCIS based on the refined latent space.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
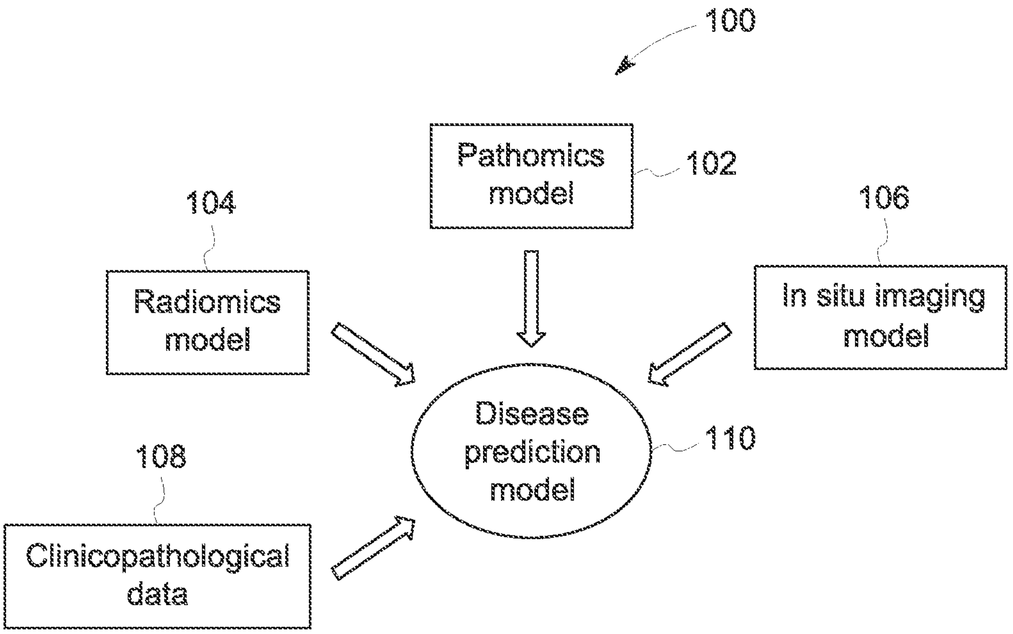
FIG. 1 is a schematic diagram of an exemplary system for detecting a recurrence of a disease in a patient, in accordance with an embodiment of the present technique.

One or more specific embodiments of the present disclosure are described below. These described embodiments are only examples of the systems and methods for locally enhancing a medical image. The skilled artisan will understand that specific details described in the embodiments can be modified when being placed into practice without deviating from the spirit of the present disclosure.

As used herein, an element or step recited in the singular and proceeded with the word "a" or "an" should be understood as not excluding plural of said elements or steps, unless such exclusion is explicitly stated. Moreover, the terms "first," "second," and "third," etc. are used merely as labels, and are not intended to impose numerical requirements or a particular positional order on their objects. Furthermore, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." As the terms "connected to," "coupled to," etc. are used herein, one object (i.e., a material, element, structure, number, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

The malignancy of breast cancer is unclear and no dominant cause has emerged; however, early detection and treatment may generate a good prognosis for the patient. In recent years, radiomics and deep learning (DL) models have made substantial progress in improving the accuracy and throughput of pathology workflow for diagnostic and prognostic prediction. These DL models are often combined with clinical data for disease risk stratification and prognosis prediction. However, fusion of information coming from different source of data is difficult. Often features from different data sources including imaging and clinical records are concatenated before prognosis prediction. Often such prediction models are not clinically interpretable and suffers from data scaling issues as features are combined from different data sources.

As explained earlier, ductal carcinoma in situ (DCIS) or stage 0 account for a significant percentage of newly diagnosed cancer cases (approximately 20-25%). Also, as explained earlier, among the breast cancer subtypes, invasive Triple negative breast cancer (TNBC) (e.g., stage 1+) is the most aggressive and heterogeneous breast cancer subtype. In the present technique, a TNBC or a DCIS recurrence prediction model is used that combines information from different data sources including mammogram, histopathology images and clinic-pathological variables to predict prognosis. In contrast to directly combining features for prediction as in conventional methods, in the present technique, the recurrence probabilities from different sources of data are used for prognosis prediction. For example, the recurrence probabilities are combined in a Bayesian learning framework to create a clinically explainable artificial intelligence (AI) model.

FIG. 1 shows a schematic diagram of an exemplary system 100 for detecting a recurrence of a disease such as an invasive Triple negative breast cancer (TNBC) in a patient, in accordance with an embodiment of the present technique. The system 100 may also be utilized to detect a recurrence of breast cancer in a patient with DCIS. System 100 shows a disease prediction model 110 that receives a plurality of inputs such as a plurality of recurrence probabilities from radiomics model 102, pathomics model 102, in situ imaging model 106 and further clinicopathological data 108 related to the patient. In one embodiment, the disease prediction model 110 includes an artificial intelligence (AI) model such as a Bayesian network that predicts recurrence of a disease e.g., invasive TNBC or DCIS.

The Pathomics model 102 is used to detect a first recurrence probability of the disease from whole slide Hematoxylin and Eosin (H&E) biopsy samples of the patient. In one embodiment, the model 102 extracts fixed image patches of predefined pixels (e.g., 224×224 or 256×256) from the whole slide H&E biopsy samples. The pathomics model further includes a pre-trained deep learning encoder to automatically map each of the fixed image patches to an initial latent space. The initial Latent space is further refined by encoding patches generated by a generative adversarial network (GAN) model that captures features of aggressive cancers. Such refinement of latent space helps identify representative features that are used in a neural-network architecture to predict the first recurrence probability as will be explained in more detail subsequently.

The radiomics model 104 detects a second recurrence probability of the disease from routine mammogram of the patient. The radiomics model 104 may detect irregular infiltration of a surrounding normal tissue around a tumor region in the form greater heterogeneity in intensity distribution by radiomic methods. For example, a plurality of radiomics features is extracted from invasive edge of breast tumors as observed in routine mammograms. The plurality of radiomics features is then analyzed to determine the second recurrence probability. The details of determining the second recurrence probability from the plurality of radiomics features has been explained in co-pending patent application filed on Mar. 25, 2022, Ser. No. 17/704,531, which is incorporated herein by reference in its entirety.

The disease prediction model 110 may further receive other plurality of disease recurrence probabilities from various other data sources such as in situ imaging model for example transcriptomics or immunohistochemistry model 106 on a small set of tissue images of the patient to determine the disease recurrence probability. The disease prediction model 110 may further receive clinicopathological data 108 related to the patient. The clinicopathological data 108 related of the patient may include age and size of a tumor and/or Lymph node positivity for example. The disease prediction model 110 will be explained in more detail subsequently.

Figure 2:
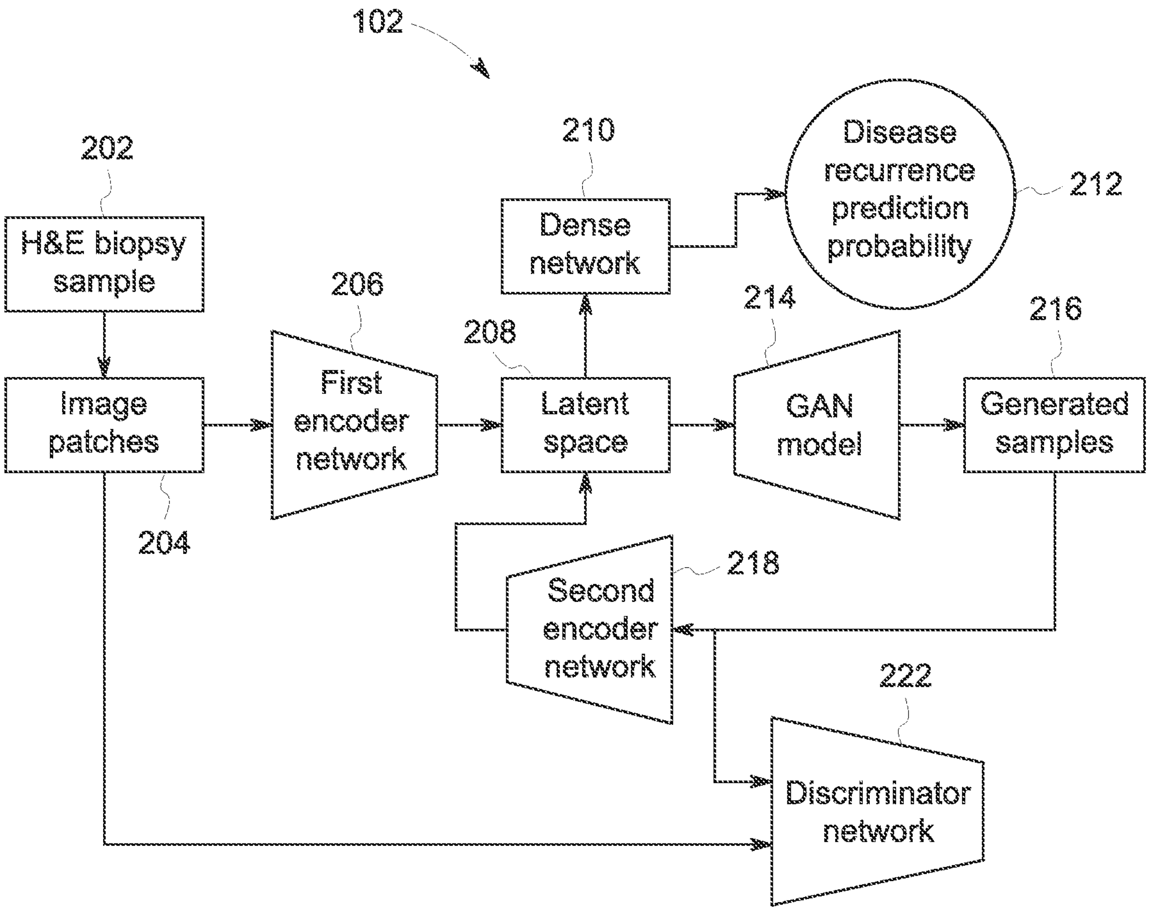
FIG. 2 is a schematic diagram of a pathomics model, in accordance with an embodiment of the present technique.
Figure 3:
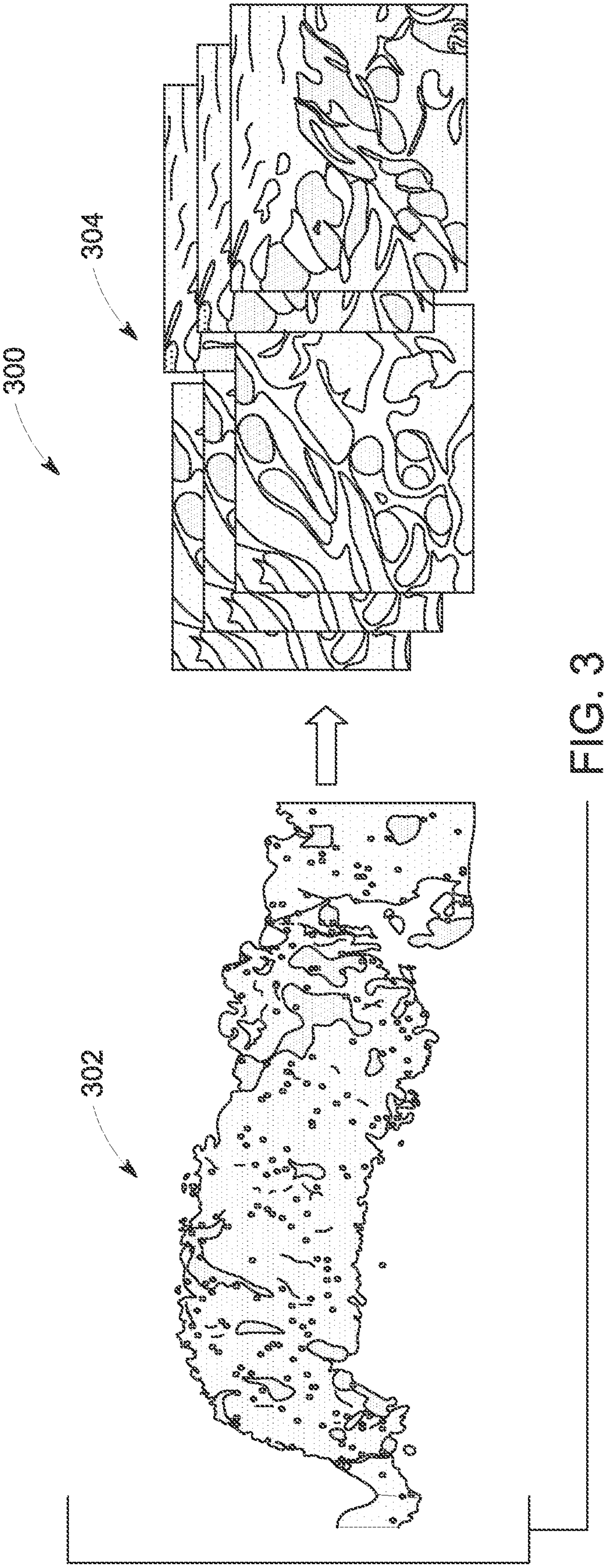
FIG. 3 is a schematic diagram of a H&E biopsy sample and a converted smaller image patches, in accordance with an embodiment of the present technique.

FIG. 2 shows a schematic diagram of a pathomics model 102 in accordance with an embodiment of the present technique. The pathomics model 102 receives H&E biopsy sample 202 of the patient as an input. The H&E biopsy samples may be a whole side H&E biopsy samples of the patient. These H&E biopsy samples 202 are large in size (e.g., 14000×9000 pixels). The pathomics model 102 splits these large H&E biopsy samples 202 into smaller image patches 204 (e.g., 224×224 pixels, 256×256 pixels, etc.). FIG. 3 shows a schematic diagram 300 of both the large H&E biopsy sample 302 and the converted smaller image patches 304.

Figure 4:
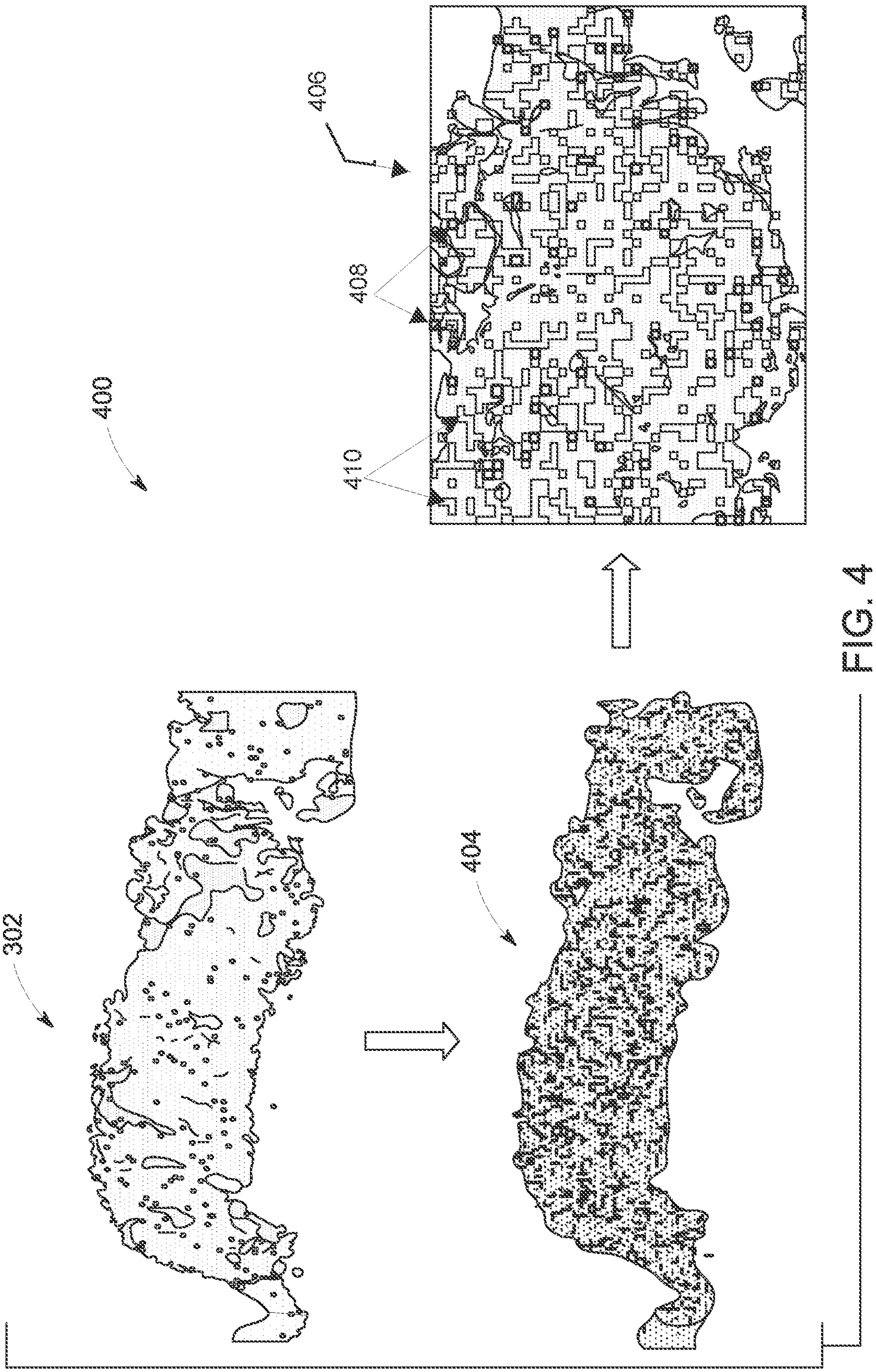
FIG. 4 is a schematic diagram of the original large H&E biopsy sample and a second biopsy image in which both the aggressive patches and non-aggressive patches classified by a dense network are mapped.

Referring back to FIG. 2, a first encoder network 206 maps each of image patches 204 into a latent space 208. As will be appreciated by those skilled in the art, in the latent space 208, images that are similar to each other are grouped together on a map. In one embodiment, the first encoder network 206 may be a deep learning (DL) network. The latent space 208 is then provided as an input to a dense network 210. In one embodiment, the dense network 210 may be another DL network that classifies the latent space data 208 into aggressive patches and non-aggressive patches and finally provides a disease recurrence probability 212 based on the aggressive and non-aggressive patches. In general, the aggressive patches are associated with high probability of disease recurrence (e.g., P>0.9) while the non-aggressive patches are associated with low probability (e.g., P<0.1). FIG. 4 shows a schematic diagram 400 of the original large H&E biopsy sample 302 and a second biopsy image 404 in which both the aggressive patches and non-aggressive patches classified by the dense network 210 are mapped. A zoomed view of second image 404 is shown in image 406. Image 406 shows the placement of aggressive patches by bold font patches 408 and non-aggressive patches by non-bold font patches 410.

Figure 5:
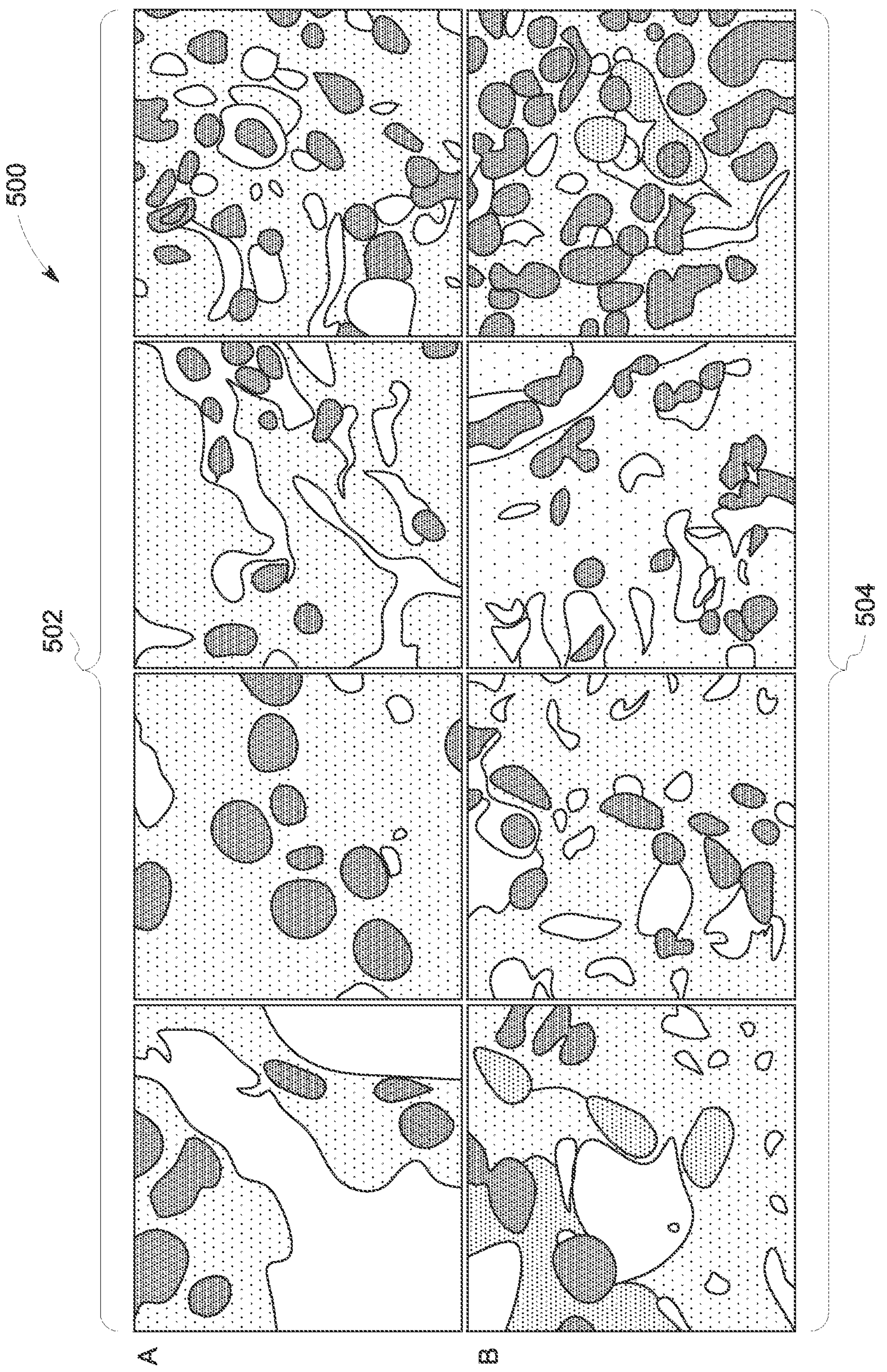
FIG. 5 is a schematic diagram of the generated synthetic image samples, in accordance with an embodiment of the present technique.

FIG. 2 also shows a Generative Adversarial Network (GAN) model 214. The GAN model 214 receives latent space data 208 as input and further generates synthetic image patches or samples 216. The synthetic image samples 216 are then provided to a second encoder network 218 which maps back the synthetic image samples to the latent space 208. This process further refines the latent space 208 that trains the dense network 210 and helps to identify representative features that differentiate recurrent from non-recurrent cancers improving on sensitivity and specificity of recurrence prediction. For example, lesions may be automatically identified as ductal carcinoma in situ (DCIS) as opposed to benign intraductal proliferations. In addition, if the lesion is DCIS, it may be stratified based on the risk of recurrence and/or progression to invasive cancer. In one embodiment, the synthetic image samples 216 are further provided to a discriminator network 224 which verifies that the generated synthetic image samples 216 are very close to the real samples i.e., image patches 204. FIG. 5 shows a schematic diagram 500 of the generated synthetic image samples. Specifically, the top images 502 represent samples with low risk of disease recurrence and the bottom images 504 represent low risk of disease recurrence.

Referring back to FIG. 1, the disease recurrence prediction probability from pathomics model 102 is provided to disease prediction model 110. The disease prediction model 110 also receives the second recurrence probability of the disease generated by the radiomics model 104 from routine mammogram of the patient and other disease recurrence probability from in situ imaging model 106. Based on the plurality of disease prediction probabilities received and clinicopathological data, the disease prediction model 110 predicts recurrence of a disease such as TNBC.

Figure 6:
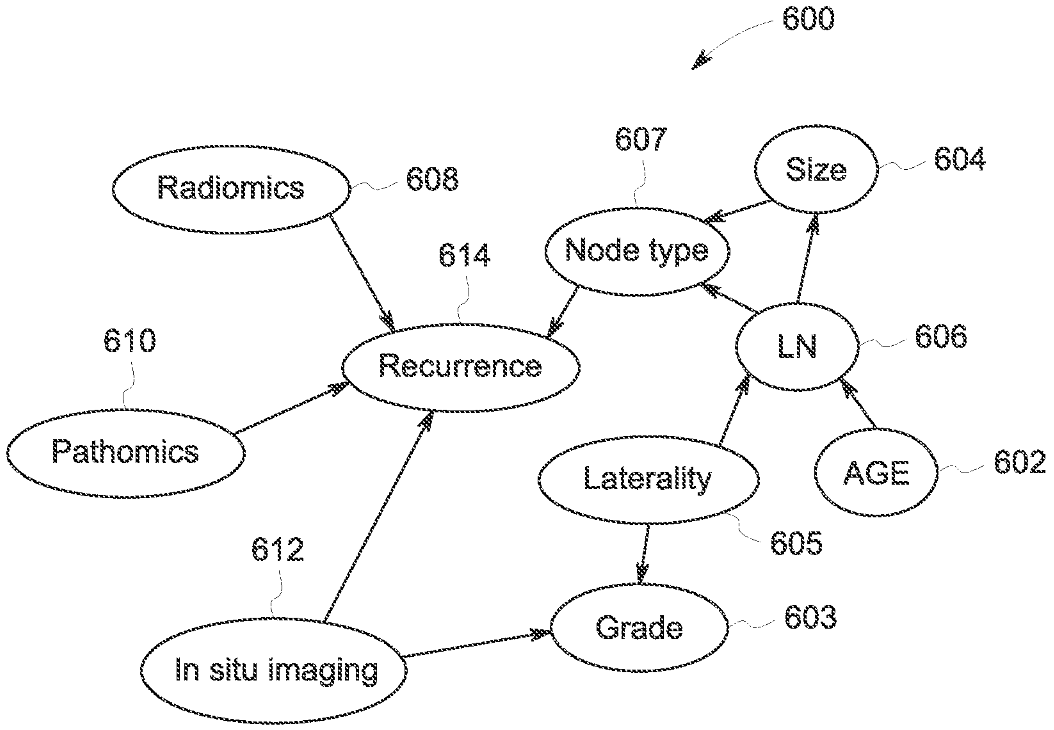
FIG. 6 is a schematic diagram of a disease prediction model, in accordance with an embodiment of the present technique.

FIG. 6 shows a schematic diagram of a disease prediction model 600, in accordance with an embodiment of the present technique. In general disease prediction model 600 represents a clinically interpretable Bayesian network framework. As will be appreciated by those skilled in the art, the Bayesian network is a graphical model represents a set of variables and their conditional dependencies. The model 600 includes variables shown by nodes 602, 604, 606, 608, 610 and 612. Nodes 602, 604 and 606 are variables representing clinicopathological data of the patient. For example, node 602 represents age of the patient and nodes 604 and 606 represents size and lymph node (LN) presence respectively. Further, nodes 608, 610 and 612 represent multiple disease recurrence probabilities obtained from various data sources. For example, node 610 represents a first prediction probability determined by a pathomics model. Similarly, node 608 represents a second prediction probability determined by a radiomics model and node 612 represents and prediction probability determined by an in situ imaging model. All these nodes have conditional probability values with respect to each other. The conditional probability represents a probability of one node being true or false if another node is true or false. For example, the conditional probability may provide that if age of a patient is more than 60 years and the probability of pathomics model is 0.9 then the chances that the second probability determined by radiomics model will be 0.9 is very high. Thus, depending on all the node probability values and conditional probabilities finally the recurrence 614 of the disease such as TNBC or DCIS may be predicted by the Bayesian network model 600.

Further, the Bayesian network 600 clearly shows conditional dependencies between a disease grade 603 and laterality 605 and between lymph node 606, patient age 602 and laterality 605. Moreover, there is another conditional dependency between lymph node 606, size 604 and node type 607. Based on the Bayesian network 600, the clinician can easily interpret that grade and size of the tumor are playing major part in the calculated disease recurrence probability 614.

Figure 7:
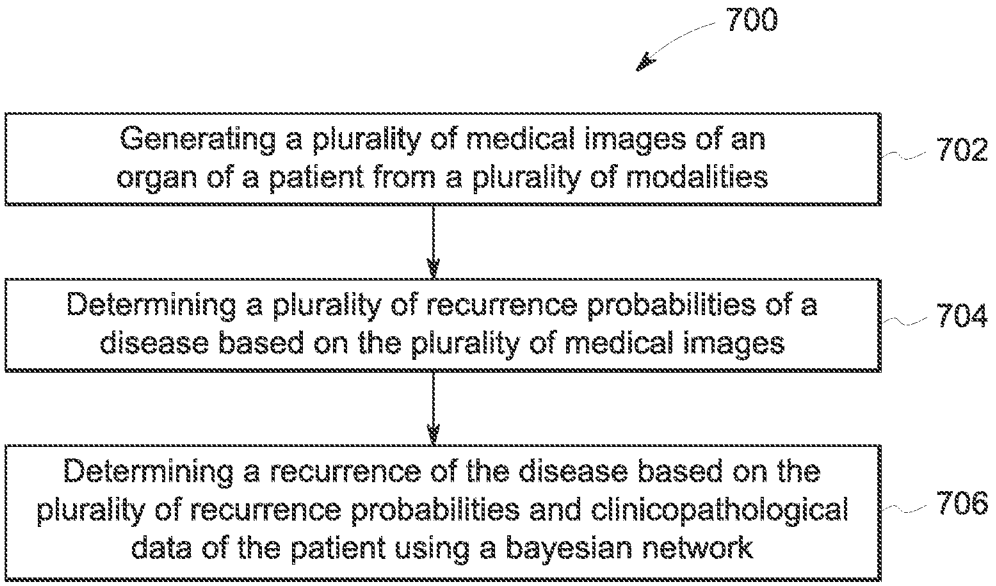
FIG. 7 is a flow chart diagram of a method for determining recurrence of a disease in a patient, in accordance with an embodiment of the present technique.

FIG. 7 shows a flow chart diagram of a method 700 for determining recurrence of a disease in a patient. In one embodiment, the disease may include triple negative breast cancer (TNBC) and/or ductal carcinoma in situ (DCIS) in a patient. The method includes generating a plurality of medical images of an organ of a patient from a plurality of modalities at step 702. The plurality of medical images may include X-ray images generated by an X-ray system, Hematoxylin and Eosin (H&E) biopsy sample images generated from Needle biopsy and in situ imaging data generated by immunohistochemistry or transcriptomics, Positron emission tomography (PET) scans images, ultrasound images and Magnetic resonance imaging (MRI) scan images or combinations thereof. In one embodiment, generating the plurality of medical images may be include using various imaging systems or acquiring the medical images from a database where the medical images are stored for the patient.

At step 704, the method includes determining a plurality of recurrence probabilities of the disease based on the plurality of medical images. As explained above a first recurrence probability of a disease may be determined by a pathomics model, a second recurrence probability may be determined by a radiomics model and third recurrence probability may be determined by in situ imaging model. As described earlier, determining the first recurrence probability includes extracting fixed image patches of predefined pixels (e.g., 224×224 or 256×256) from the whole slide H&E biopsy samples and automatically mapping each of the fixed image patches to an initial latent space. The initial Latent space is further refined by encoding patches generated by a generative adversarial network (GAN) model that captures features of aggressive cancers. Such refinement of latent space helps in identifying representative features that are used in a neural-network architecture to predict the first recurrence probability. For example, the latent space may be utilized to help in automatically identifying lesions as ductal carcinoma in situ (DCIS) as opposed to benign intraductal proliferations. In addition, if the lesion is DCIS, it may be stratified based on the risk of recurrence and/or progression to invasive cancer as determined by the neural-network architecture. The second recurrence probability is determined from routine mammogram of the patient. In one embodiment, the method includes detecting irregular infiltration of a surrounding normal tissue around a tumor region in the form greater heterogeneity in intensity distribution using radiomic methods. For example, a plurality of radiomics features is extracted from invasive edge of breast tumors as observed in routine mammograms. The plurality of radiomics features is then analyzed to determine the second recurrence probability.

The third disease recurrence probability may be determined based on in situ imaging on a small set of tissue images of the patient. Finally, at step 706, the method includes using a Bayesian network for determining a recurrence of the disease in the patient based on the plurality of recurrence probabilities and clinicopathological data of the patient. The clinicopathological data of the patient may include age and size of a tumor and/or lymph node positivity, for example. The plurality of recurrence probabilities and clinicopathological data values represent nodes in the Bayesian network. Thus, the Bayesian network determines the final disease recurrence, depending on all the node probability values and conditional probabilities between the nodes.

As an example, the system 100 in FIG. 1 and, in particular, the pathomics model 102 may be utilized for recurrence prediction in ductal carcinoma in situ (DCIS) patients. Samples were analyzed for a cohort of 68 DCIS patients. The patients were aged between 35 to 89 years. The lesion sizes ranged from 5 to 90 millimeters (mm). The cases includes a mixed of low (15%), intermediate (35%), and high (50%) grade cases. Patients were treated with mastectomy and/or a combination of lumpectomy, radiation, and hormone therapy. Tissue microarrays (TMAs) were constructed from 2 mm cores (1-3 cores per patient) in conjunction with a breast pathologist to create H&E images for further analysis. The cohort was split into independent training (n=50 patients, 10 patients with reoccurrences at 5 years) and validation groups (n=18 patients, 6 patients with recurrence at 5 years). Tiles of 256×256 pixels were extracted from whole slide pathological images (H&E) (e.g., at 20× resolution) to train a GAN to generate image patches. A total of over 200,000 patches were used for training and the AI model was validated using 30,000 patches. A pretrained deep learning architecture was used as a mapping/encoding network to automatically map each of the patches to an initial latent space. The latent space is further refined be encoding patches generated by the GAN model to capture features of aggressive cancers. Such refinement of latent space helps to automatically identify representative features that differentiate recurrent from non-recurrent cancers, thus, improving on sensitivity and specificity of recurrence prediction. In particular, clusters were found in the density plots from the latent space that directly correspond to tissue patches. Aggressive patches (e.g., from aggressive clusters) generated from the GAN model along with the TMA (H&E) image patches were utilized to train a deep learning classification network (e.g., Inception-ResNet-v2). The ability to generate synthetic image patches of aggressive lesions permitted training of a large DL classification network and to predict recurrence in DCIS patients (without needing manual annotation for the process). The GAN model identifies DCIS in an unsupervised manner and uses its features to define/predict risk of aggressiveness.

The DL classification model trained with both TMA (H&E) images and GAN generated patches predicted recurrence with a mean area under curve (AUC) of 0.87, a sensitivity of 0.83, and a specificity of 0.91 in the validation set. The DL classification model trained from TMA (H&E) images only predicted recurrence with an AUC of 0.81. The utilization of the GAN model to generate H&E images circumvents the need for a large cohort and accurate labor-intensive manual annotation of histopathological images, which is often required for training a deep learning classification model. The use of GAN generate aggressive image patches during training significantly improves recurrence prediction accuracy of the deep learning classification model.

Figure 8:
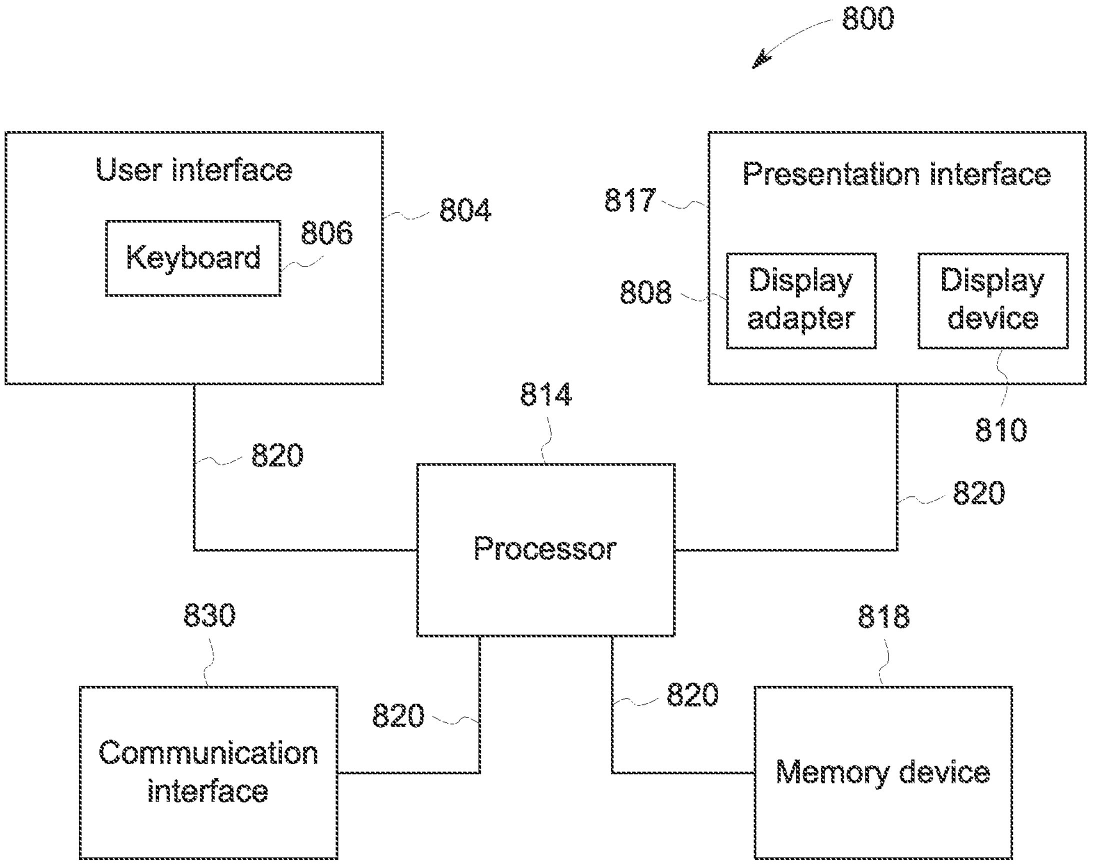
FIG. 8 is a block diagram of an exemplary computing device, in accordance with an embodiment of the present technique.

The radiomics model 104, pathomics model 102, in situ imaging model 106, disease prediction model 110 and some of the steps of method 700 described herein may be implemented on any suitable computing device 800 and software implemented therein. FIG. 8 is a block diagram of an exemplary computing device 800. In the exemplary embodiment, the computing device 800 includes a user interface 804 that receives at least one input from a user. The user interface 804 may include a keyboard 806 that enables the user to input pertinent information. The user interface 804 may also include, for example, a pointing device, a mouse, a stylus, a touch sensitive panel (e.g., a touch pad and a touch screen), a gyroscope, an accelerometer, a position detector, and/or an audio input interface (e.g., including a microphone).

Moreover, in the exemplary embodiment, computing device 800 includes a display interface 817 that presents information, such as input events and/or validation results, to the user. The display interface 817 may also include a display adapter 808 that is coupled to at least one display device 810. More specifically, in the exemplary embodiment, the display device 810 may be a visual display device, such as a cathode ray tube (CRT), a liquid crystal display (LCD), a light-emitting diode (LED) display, and/or an "electronic ink" display. Alternatively, the display interface 817 may include an audio output device (e.g., an audio adapter and/or a speaker) and/or a printer.

The computing device 800 also includes a processor 814 and a memory device 818. The processor 814 is coupled to the user interface 804, the display interface 817, and the memory device 818 via a system bus 820. In the exemplary embodiment, the processor 814 communicates with the user, such as by prompting the user via the display interface 817 and/or by receiving user inputs via the user interface 804. The term "processor" refers generally to any programmable system including systems and microcontrollers, reduced instruction set computers (RISC), complex instruction set computers (CISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, the memory device 818 includes one or more devices that enable information, such as executable instructions and/or other data, to be stored and retrieved. Moreover, the memory device 818 includes one or more computer readable media, such as, without limitation, dynamic random access memory (DRAM), static random access memory (SRAM), a solid state disk, and/or a hard disk. In the exemplary embodiment, the memory device 818 stores, without limitation, application source code, application object code, configuration data, additional input events, application states, assertion statements, validation results, and/or any other type of data. The computing device 800, in the exemplary embodiment, may also include a communication interface 830 that is coupled to the processor 814 via the system bus 820. Moreover, the communication interface 830 is communicatively coupled to data acquisition devices.

In the exemplary embodiment, the processor 814 may be programmed by encoding an operation using one or more executable instructions and providing the executable instructions in the memory device 818. In the exemplary embodiment, the processor 814 is programmed to select a plurality of measurements that are received from data acquisition devices.

In operation, a computer executes computer-executable instructions embodied in one or more computer-executable components stored on one or more computer-readable media to implement aspects of the invention described and/or illustrated herein. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

One of the advantages of the present technique is that it can predict TNBC and/or DCIS recurrence from routine mammograms, biopsy sample and clinic-pathological variables. The technique be also used for cancer risk stratification for other cancers including prostate, lung and glioblastoma.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the subject matter set forth herein without departing from its scope. While the dimensions and types of materials described herein are intended to define the parameters of the disclosed subject matter, they are by no means limiting and are exemplary embodiments. Many other embodiments will be apparent to those of skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for determining a recurrence of a ductal carcinoma in situ (DCIS) in a patient, the method comprising:

generating a plurality of medical images of breast tissue of the patient;

determining a plurality of recurrence probabilities from the plurality of medical images, wherein the plurality of recurrence probabilities includes a first recurrence probability, a second recurrence probability and a third recurrence probability, wherein the first recurrence probability is determined from H&E biopsy sample images, wherein determining the first recurrence probability comprises extracting fixed image patches of predefined pixels from the H&E biopsy sample images, wherein determining the first recurrence probability further comprises automatically mapping each of the fixed image patches to an initial latent space, wherein determining the first recurrence probability further comprises refining the initial latent space to generate refined latent space by encoding patches generated by a generative adversarial network (GAN) model that captures features of aggressive DCIS, and wherein determining the first recurrence probability further comprises using a deep learning (DL) network to classify the refined latent space into aggressive patches and non-aggressive patches and to predict the first recurrence probability based on the aggressive patches and non-aggressive patches; and determining a recurrence of the DCIS based on the plurality of recurrence probabilities and clinicopathological data of the patient using a Bayesian network.

2. The method of claim 1, wherein the plurality of medical images comprises X-ray images, Hematoxylin and Eosin (H&E) biopsy sample images, molecular images, Positron emission tomography (PET) scans images, ultrasound images, Magnetic resonance imaging (MRI) scan images or combinations thereof.

3. The method of claim 1, wherein the second recurrence probability is determined from routine mammogram images of the patient.

4. The method of claim 3, wherein determining the second recurrence probability comprises extracting and analyzing a plurality of radiomics features from an invasive edge surrounding the disease observed in routine mammogram images.

5. The method of claim 1, wherein the third recurrence probability is determined based on in situ imaging on a small set of tissue images of the patient.

6. The method of claim 1, wherein the clinicopathological data of the patient includes age, size, location, laterality and Lymph node positivity of the disease.

7. The method of claim 6, wherein the plurality of recurrence probabilities and clinicopathological data values represent a plurality of nodes in the Bayesian network and the Bayesian network determines the DCIS recurrence, depending on the node probability values and conditional probabilities between the nodes.

* * * * *